Oct. 5, 1971 G. MERRILL Plant Pat. 3,064
NECTARINE
Filed Oct. 31, 1969
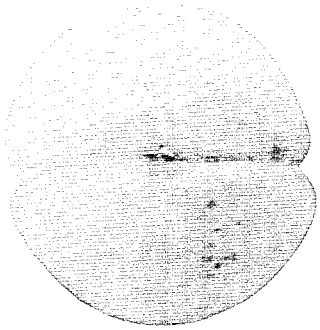
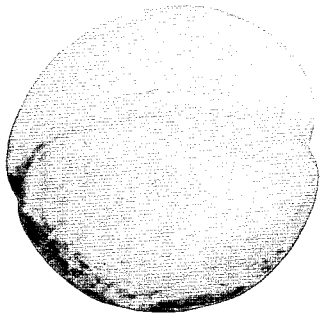
GRANT MERRILL
INVENTOR
Vergil L. Gerard
ATTORNEY

United States Patent Office

Plant Pat. 3,064
Patented Oct. 5, 1971

3,064

NECTARINE

Grant Merrill, 416 N. Anderson Road, Exeter, Calif. 93221

Filed Oct. 31, 1969, Ser. No. 873,142
Int. Cl. A01h *5/03*
U.S. Cl. Plt.—41 1 Claim

The present invention relates to a nectarine tree and more particularly to a new and improved variety thereof broadly characterized by very early ripening fruit which has a very red color, is relatively large in size and has very firm flesh, and by its blossoms which bloom relatively early, which make the variety well adapted to growing in areas of relatively early production, and by its heavy and regular bearing, vigorous growing tree.

The instant variety most nearly resembles the Sunbright variety of nectarine (U.S. Plant Patent 2138), but differs therefrom and is an improvement thereon in that it bears fruit having a more glossy, waxy red colored skin with less russet, has blossoms which bloom earlier and bears heavier and more regular fruit.

I discovered the present variety by growing seeds of the Merrill Queen Nectarine (U.S. Plant Patent 2010), open pollinated, by mean of embryo-culture, on a farm in Exeter, Tulare County, Calif. The new variety of nectarine has been essentially reproduced by budding and grafting a number of test trees in various places in Tulare County and in each case the resulting tree and fruit characteristics were those of the original tree.

The accompanying drawing is an oil painting of a characteristic fruit showing the skin color, flesh color, and shape. All major color plate indentifications are by reference to Maerz and Paul Dictionary of Color, First Edition.

Referring now more specifically to the pomological characteristics of this new and distinct variety of nectarine tree, the following has been observed under the ecological conditions prevailing in Tulare County, Calif.

*Tree*

Production character: Large size tree, heavily productive, regular bearing.

Trunk: Medium size, gray in color, shaggy.

Branches: Medium size, gray and shaggy on older branches, brown and smoother on young branches.

Lenticels: Medium size, numerous.

Leaves: (Taken from mid portion of vigorous upright shoots.) Medium size; larger leaves 6¼ to 7¼ inches long, 15/16 to 1¼ inches wide; shape, lanceolate; tip, acuminate; color upper surface—dark green, lower surface—lighter green, veins on lower surface—very light yellow green; margin, crenate, glandular; glands, 3–7 in number, alternate, medium size, reinform, positioned at base of leaf and on petiole; stipules, present on young leaves, dropping off early; class (Meador and Blake, American Society for Horticultural Science, volume 37, pages 203–207), mostly 2, some 3.

*Flower buds*

Medium size, plump, publescent, free.

*Flowers*

Blooms: Showy, large, pink, pollen abundant.

Season: Medium Early with Elberta (unpatented); first blossoms about Feb. 26, full bloom about Mar. 4, 1968.

An Early seasons for blooms. About the same as Sunbright Nectarine (U.S. P.P. 2138) on young trees and young grafts (about June 10, 1968). On fully mature trees or graft, about one week earlier than Sunbright Nectarine.

*Fruit*

Maturity: First week in June.

Shape: Large for its season, generally oval, axial diameter 2¼ to 2⅝ inches, transverse in suture plane—2⅛ to 2½ inches.

Suture: Distinct shallow line extending from base to apex with slight depression beyond pistil point in some fruit.

Ventral surface: Rounded, slightly lipped on both sides on most fruit, lips both equal and unequal.

Dorsal surface: Slight groove on most fruit.

Cavity: Oval, elongated in suture plane with suture showing on both sides, depth 3/16 to 5/16 inches, breadth about ¾ inch.

Base: Retuse.

Apex: Pistil point apical, small.

Stem: ⅛ to ¼ inch long, about ⅛ inch diameter.

Skin: Medium thin, medium tender, tenacious to flesh, tendency to crack-slight, down-none; color, undercolor, sunflower yellow Plate 9 L–4, to cadmium yellow Plate 9 L–8, overlaid with paprika red Plate 2 J–12 to Scarlet Plate 1 L–12 with blotches of Burmese Ruby Plate 7 H–6.

Flesh: Amygdalin, moderate; juice, abundant; texture, fine and meaty to melting; fibers, fine, tender; ripens slightly sooner on apex and near skin; color, yellowish green Plate 19 L–4 next to the stone, light yellow Plate 9 L–1 from the center outwardly, graduating to a deep chrome yellow Plate 9 L–7 in the center portion of the flesh, cadmium yellow Plate 9 L–8 nearer the skin.

Eating quality: Good, aroma slight.

*Stone*

Generally: Slightly free when ripened off the tree, cling when firm or hard.

Fibers: Short, fine.

Size: Generally 1⅛ to 1⅜ inches long, ⅞ to 1 1/16 wide, ⅝ to ⅞ inch thick.

Form: Generally obovate with some nearly oval, with tip acuminate.

Base: Generally straight.

Hilum: Oval.

Apex: Acuminate.

Sides: Both equal and unequal, some sides quite flat.

Surface: Irregularly furrowed and with a few pits toward apex, pitted and a few furrows toward base; pits circular, some elongated.

Ventral edge: Thick with many small grooves.

Dorsal edge: Generally with deep groove toward middle and base.

Color of stone: Reddish brown when fresh, tan to brown when dry.

*Use*

General: Local fresh use and long distant shipment.

Keeping quality: Good.

Shipping quality: Good.

Although my new variety of nectarine possesses the described characteristics under the growing conditions in Tulare County, Calif., having first been observed there, it is to be understood that variations of the usual magnitude in characteristics incident to the growing conditions, fertilization, pruning and pest control are to be expected.

Having thus described and illustrated my new variety of nectarine tree, what is claimed is:

1. A new and distinct variety of nectarine substantially as illustrated and described, which is characterized by a heavily productive and regular bearing tree producing very easily ripening fruit with red waxy skin which is large for its season; and which most nearly resembles Sunbright nectarine, U.S. Plant Patent 2,138, but is distinguished therefrom in bearing more heavily and regularly, in blooming earlier making it better adapted to areas of warmer winters, and in bearing fruit which is redder, waxier, and has less russet.

No references cited.

ROBERT E. BAGWILL, Primary Examiner